(12) United States Patent
Yoon et al.

(10) Patent No.: US 8,707,809 B2
(45) Date of Patent: Apr. 29, 2014

(54) MULTI-SELECTIVE MICRO MANIPULATOR

(75) Inventors: Eui Sung Yoon, Seoul (KR); Sung Wook Yang, Gyeonggi-do (KR); Jinseok Kim, Seoul (KR); Duk moon Rho, Seoul (KR); JeiWon Cho, Gyeonggi-do (KR); Hee Sup Shin, Gyeonggi-do (KR)

(73) Assignee: Korea Institute of Science and Technology, Seoul (KR)

( * ) Notice: Subject to any disclaimer, the term of this patent is extended or adjusted under 35 U.S.C. 154(b) by 1167 days.

(21) Appl. No.: 12/641,083

(22) Filed: Dec. 17, 2009

(65) Prior Publication Data

US 2011/0100147 A1    May 5, 2011

(30) Foreign Application Priority Data

Oct. 29, 2009 (KR) .................. 10-2009-0103753

(51) Int. Cl.
*A61B 5/05*         (2006.01)
(52) U.S. Cl.
USPC .............................. 74/57; 74/126; 600/544
(58) Field of Classification Search
USPC ............................ 74/57, 126, 826; 600/544
See application file for complete search history.

(56) References Cited

U.S. PATENT DOCUMENTS

| 6,057,682 A * | 5/2000 | McCurley et al. ......... 74/473.12 |
| 7,370,551 B2 * | 5/2008 | Tokuo et al. ............... 74/473.12 |
| 7,721,615 B2 * | 5/2010 | Ehrlich et al. .................. 74/335 |

FOREIGN PATENT DOCUMENTS

| GB | 2 394 261 | * 4/2004 |
| JP | 07-198314 | 8/1995 |
| JP | 2000-060817 | 2/2000 |
| KR | 10-0608998 | 8/2006 |

OTHER PUBLICATIONS

Yang, S. et al., "Piezo Motor Based Microdrive for Neural Signal Recording," *30th Annual International IEEE EMBS Conference*, Aug. 20-24, 2008, pp. 3364-3367, Vancouver, British Colombia, Canada.

* cited by examiner

*Primary Examiner* — William C Joyce
(74) *Attorney, Agent, or Firm* — Fenwick & West LLP

(57) ABSTRACT

The multi-selective micromanipulator has a main mover which moves linearly or rotationally with respect to an axis, an actuator which moves the main mover, a projection which is formed on the main mover, and a plurality of submovers which the projection selectively contacts depending on the movement of the main mover, wherein a selected submover is linearly moved by the projection in a direction parallel to the axis direction.

14 Claims, 15 Drawing Sheets

MULTI-SELECTIVE MICRO MANIPULATOR

CROSS-REFERENCE TO RELATED APPLICATION

This application claims priority under 35 U.S.C. §119(a) to Republic of Korea Patent Application No. 10-2009-0103753, filed on Oct. 29, 2009, and all the benefits accruing therefrom, the contents of which in its entirety are herein incorporated by reference.

BACKGROUND

1. Field

This disclosure relates to a micromanipulator, more particularly to a multi-selective micromanipulator capable of controlling the motion of a main mover using a single actuator to linearly move a plurality of submovers selectively.

2. Description of the Related Art

A living organism consists of numerous nerve cells, which mediate transmission of information. The transmission of information between the nerve cells is achieved by sending and receiving of electrical signals. That is, the nerve cells transmit information to other nerve cells by means of specific electrical signals. This also means that the nerve cells are sensitive to external electrical stimulations.

Electrophysiology is the discipline that studies the relationship between living organisms and electricity. In other words, electrophysiology involves the study of the effect of electricity on living organisms and the electrical phenomena occurring in living organisms. Electrophysiology is making rapid progress with the development of electronic engineering, implantation of electrodes into living organisms, or the like.

Usually, small animals such as mouse are used in experiments to investigate the relationship between nerve cells and electricity. A micromanipulator is used to approach an electrode, which detects electrical signals from the nerve cells of a subject or applies electrical signals to the nerve cells, to the nerve cells.

FIG. 1 schematically illustrates an experimental apparatus used to investigate the relationship between brain nerve cells of a mouse subject and electricity. On the head of a mouse, a micromanipulator 1 which inserts an electrode into the subject is connected to analyze electrical signals from the brain. The micromanipulator 1 is connected to an external signal processor 2. The external signal processor 2 is composed of a controller which controls the motion of the micromanipulator 1, a signal processor which converts an electrical signal from the brain nerve cell into a digital signal and analyzes it, or the like.

As illustrated in FIG. 1, since the micromanipulator 1 is directly fixed to the body of the subject, it needs to have a small size so as not to constrain the motion of the subject. Accordingly, in a micromanipulator module, it is usual to use one actuator to move one electrode.

However, it may be needed to insert a plurality of electrodes at a test site of the subject. In this case, a plurality of micromanipulator modules as many as the electrodes are required to control the motion of the inserted electrodes.

But, since the area of the implanted site is limited, it is difficult to insert a plurality of electrodes at the implanted site when a plurality of micromanipulator modules are used. In addition, as the number of the modules increases, so does the number of actuators to move the electrodes, sensors, or the like. Therefore, to use a plurality of micromanipulators is inefficient in several aspects, including the weight of the apparatus, control, or the like.

SUMMARY

This disclosure is directed to providing a multi-selective micromanipulator capable of controlling the motion of a main mover to linearly move a plurality of submovers selectively. Further, it is directed to providing a multi-selective micromanipulator capable of precisely controlling the location of a plurality of electrodes even with a simple structure.

In an aspect, there is provided a multi-selective micromanipulator including a main mover which moves linearly or rotationally with respect to a certain axis, a driving means which moves the main mover, a lever which is formed on the main mover, and a plurality of submovers which the lever contacts with selectively depending on the movement of the main mover. A selected submover is linearly moved by the lever in a direction parallel to the axis direction.

The driving means may include an actuator having a shaft, the main mover may be clamped on the shaft, and the plurality of submovers may be aligned radially around the shaft.

The main mover may have a cylindrical shape, the driving means may include a guide groove formed at a surface of the main mover and a first guide pin which may be engaged with the guide groove, the guide groove may include a plurality of first inclined grooves formed to be inclined right downwardly with respect to a length direction of the shaft and a plurality of second inclined grooves formed to be inclined left downwardly with respect to the length direction of the shaft, the first inclined grooves and the second inclined grooves may be alternately aligned at the side surface of the main mover, and a first inclined groove and a second inclined groove adjacent to each other may be connected to each other to form a sawtooth-shaped guide pin path.

The first guide pin may be located above the submover, the guide groove further may include a plurality of first straight grooves formed in parallel with the length direction of the shaft, and one end of the first straight groove may be connected to an intersection of the first inclined groove and the second inclined groove formed at an upper portion of the main mover and the other end may be formed toward an upper end of the main mover to form an upper entrance through which the first guide pin may enter the intersection of the first inclined groove and the second inclined groove.

The plurality of submovers may be aligned at regular intervals.

The plurality of first straight grooves may be aligned at regular intervals.

The lever may be located in a straight line with the first straight groove.

As the main mover moves linearly downward while the lever is located above the submover, the lever may press an upper end of the submover so that the submover may be moved linearly downward.

A second guide pin located below the submover may be provided, the guide groove may further include a plurality of second straight grooves formed in parallel with the length direction of the shaft, and one end of the second straight groove may be connected to an intersection of the first inclined groove and the second inclined groove formed at a lower portion of the main mover and the other end may be formed toward a lower end of the main mover to form a lower entrance through which the second guide pin may enter the intersection of the first inclined groove and the second inclined groove.

The plurality of first second grooves may be aligned at regular intervals.

As the main mover moves linearly upward while the projection is located below the submover, the projection may lift a lower end of the submover so that the submover may be moved linearly upward.

The actuator may include a piezo motor.

The plurality of submovers may include electrodes for detecting electrical signals, and the electrodes may extend in a direction parallel to the linear moving direction of the main mover.

The plurality of submovers may have a plate-shaped head and a body having a diameter smaller than that of the head and extending perpendicularly to the head, and as the main mover moves linearly upward while the projection is located below the submover, the projection may lift the head of the submover so that the submover may be moved linearly upward.

The multi-selective micromanipulator may further include a position sensing device which senses the location of the main mover, and the position sensing device may include a magnet fixed to the main mover and a magnetic sensor which senses the location of the magnet.

In accordance with the disclosure, the motion of a main mover may be controlled using a single actuator to linearly move a plurality of submovers selectively. Accordingly, the number of actuators needed to linearly move the plurality of submovers is minimized. Consequently, the multi-selective micromanipulator may have simple structure and small size.

Further, because the motion of the submovers may be controlled precisely, the micromanipulator may be used to move electrodes whose locations should be precisely controlled.

BRIEF DESCRIPTION OF THE DRAWINGS

The above and other aspects, features and advantages of the disclosed exemplary embodiments will be more apparent from the following detailed description taken in conjunction with the accompanying drawings.

DETAILED DESCRIPTION

Figure 1:
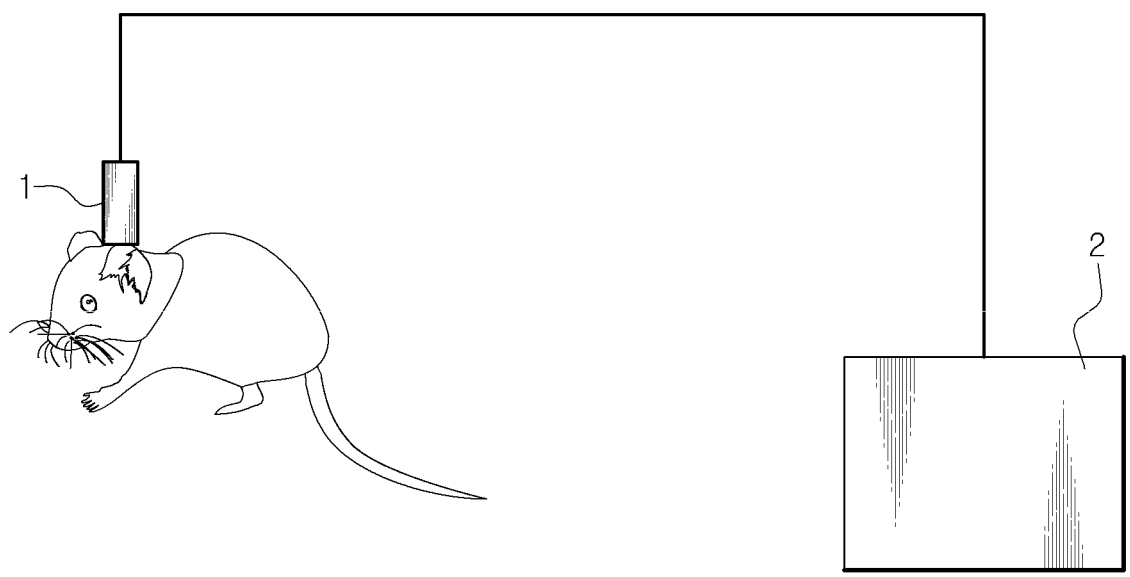
FIG. 1 schematically illustrates an experimental apparatus used to investigate the relationship between brain nerve cells of a mouse subject and electricity.

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. The use of the terms "first", "second", and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals in the drawings denote like elements. The shape, size and regions, and the like, of the drawing may be exaggerated for clarity.

Figure 2:
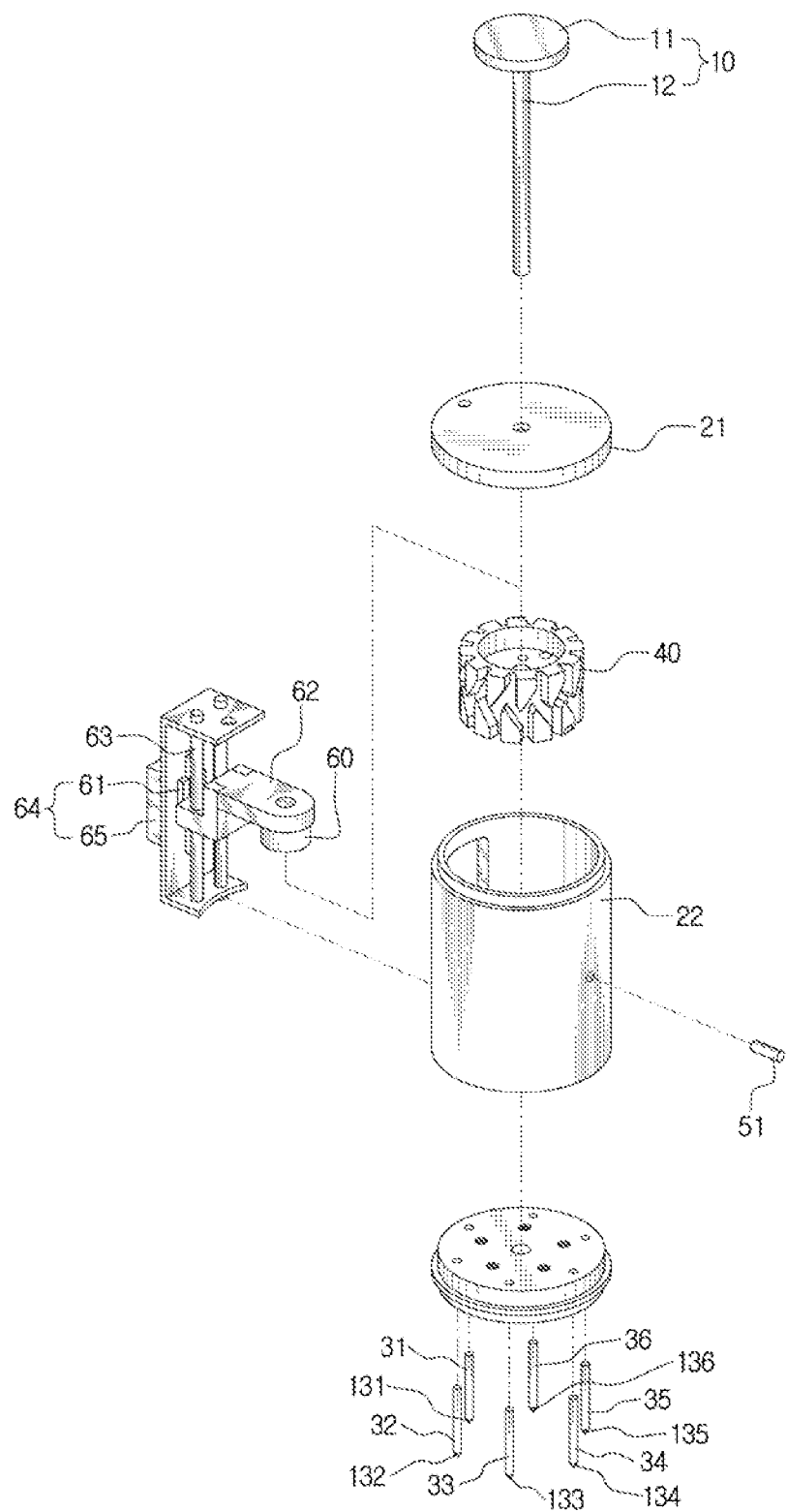
FIG. 2 is an exploded perspective view of a micromanipulator according to an embodiment.
Figure 3:
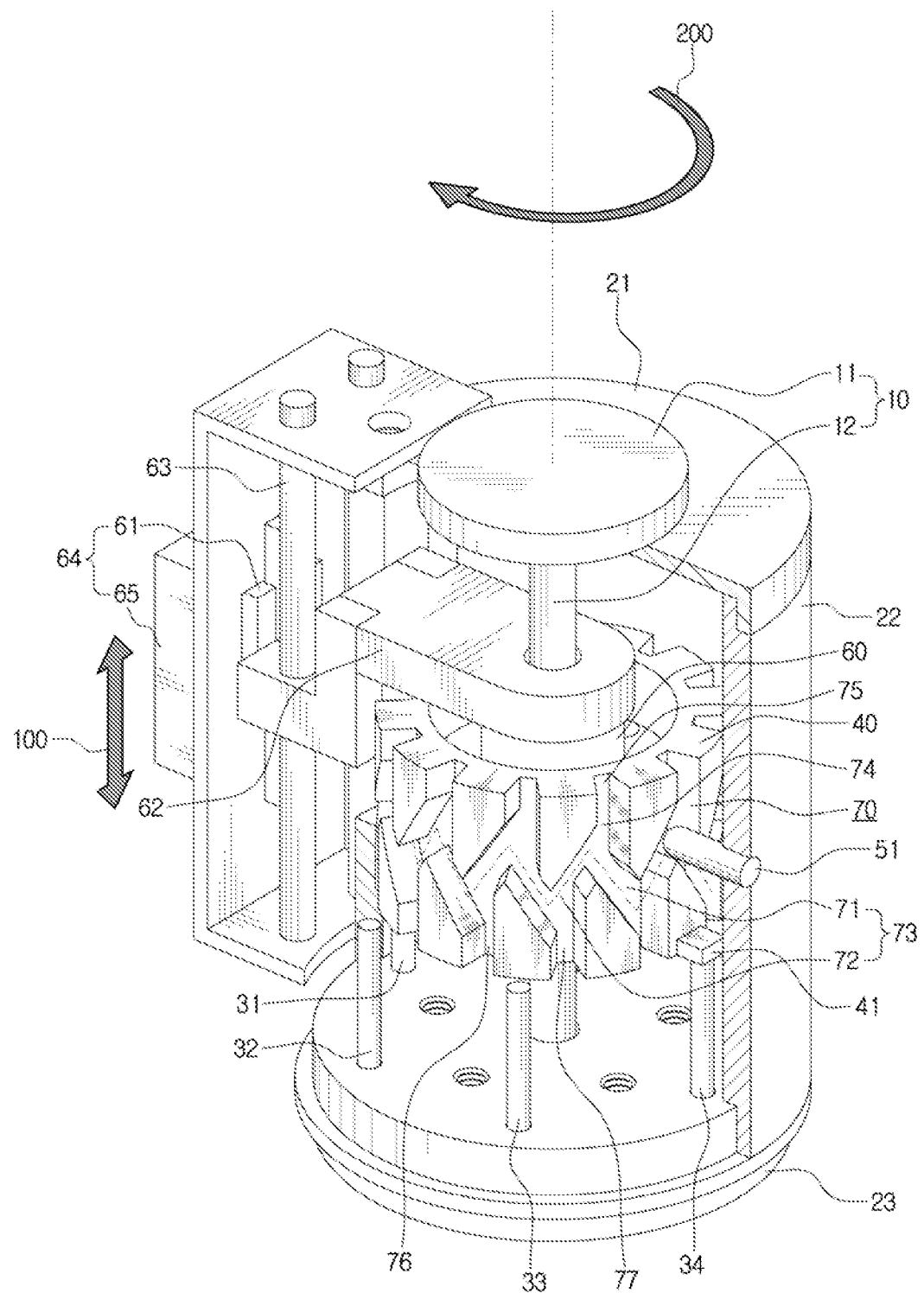
FIG. 3 is an assembled perspective view of a micromanipulator according to an embodiment.

FIG. 2 is an exploded perspective view and FIG. 3 is an assembled perspective view of a micromanipulator according to an embodiment. In FIG. 3, a case 21, 22 is partly cut open to show inside of the micromanipulator.

Referring to FIG. 2 and FIG. 3, a micromanipulator according to an embodiment comprises a cylindrical main mover 40 and a driving means for moving the main mover 40.

In an embodiment, the driving means includes a piezo motor comprising a vibrator 11 and a shaft 12. The piezo motor is used as an actuator to move the main mover 40. When an external power is applied to the piezo motor, the vibrator 11 made of a piezoelectric material undergoes a mechanical deformation and thereby vibrates the shaft 12. Then, the main mover 40 clamped on the shaft 12 is linearly moved by inertia.

The specific construction of the piezo motor and the principle by which the main mover 40 is linearly moved are well known to those skilled in the art. Therefore, a detailed description thereof will be omitted.

In this embodiment, the main mover 40 is clamped on the shaft 12. When the piezo motor 10 operates, the main mover 40 is linearly moved by the shaft 12. That is, the main mover 40 moves linearly along an axis formed by the shaft 12. Because of the operation characteristics of the piezo motor 10, the main mover 40 moves linearly, not rotationally.

The piezo motor 10 and the main mover 40 are provided in a case 21, 22, 23. Although not illustrated in detail in the figure, the shaft 12 of the motor 10 penetrates central parts of an upper case 21 and a lower case 23. As the motor 10 penetrates the centers of the upper and lower cases 21, 23, the center of mass of the micromanipulator lies at the central part and its structure is stabilized. In addition, the dimension of the micromanipulator in a traverse direction is reduced.

The shaft 12 is fixed to the upper and lower cases 21, 23 by using epoxy or the like at the intersections. That is to say, the shaft 12 is fixed to the upper and lower cases with such a strength that it may minutely vibrate upward and downward, rather than rigidly.

As such, when the piezo motor 10 is operated, the main mover 40 accommodated in the case 22 is linearly moved upward and downward by the shaft 12.

According to this embodiment, a plurality of submovers 31, 32, 33, 34, 35, 36 is selectively moved by the main mover 40. In an embodiment the submovers may be include a plurality of electrodes 131 to 136 for detecting electrical signals.

As illustrated in FIG. 2 and FIG. 3, the plurality of electrodes 131 to 136 attached on the submovers 31 to 36 extend in a direction parallel to a linear moving direction 100 of the main mover 40. The plurality of submovers 31 to 36 penetrate the lower case 23 and may move linearly upward and downward with respect to the lower case 23. The plurality of submovers 31 to 36 including electrodes 131 to 136 are aligned radially around the shaft 12.

Referring to FIG. 3, a projection 41 protrudes at a lower portion of the surface of the main mover 40. In an embodiment, the projection 41 is a rectangular plate. As the main mover 40 moves downward, the bottom of the projection 41 presses the upper end of the submover, so that the electrode attached on the submover is linearly moved downward.

In this embodiment, the main mover 40 has one projection 41. Therefore, in order to select a desired submover to move it linearly, it is needed to rotate the main mover 40 with respect to the shaft 12 and move the projection 41 right above the submover.

As described, the piezo motor 10 is an actuator which linearly moves the main mover 40 in the vertical direction 100. Therefore, in this embodiment, the driving means further comprises a rotational driver to rotate the main mover 40.

Referring again to FIG. 3, the driving means includes a guide groove 70 formed at a surface of the main mover 40, and a first guide pin 51 which may be engaged with the guide groove 70.

In this embodiment, the first guide pin 51 is inserted into the case 22 through a formed hole. The first guide pin 51 extends in a direction perpendicular to the shaft 12. The first guide pin 51 is located above the upper ends of the submovers 31 to 36.

The guide groove 70 comprises a plurality of first inclined grooves 71 formed to be inclined right downwardly with respect to a length direction of the shaft 12, and a plurality of second inclined grooves 72 formed to be inclined left downwardly with respect to the length direction of the shaft 12. As illustrated in FIG. 3, the first inclined grooves 71 and the second inclined grooves 72 are alternately aligned at the side surface of the main mover 40. A first inclined groove 71 and a second inclined groove 72 adjacent to each other are connected to each other to form a sawtooth-shaped guide pin path 73, as represented by a broken line in FIG. 3.

The guide groove 70 further comprises a plurality of first straight grooves 74 formed in parallel with the length direction of the shaft 12. One end of the first straight groove 74 is connected to an intersection of the first inclined groove 71 and the second inclined groove 72 formed at an upper portion of the main mover 40. The other end of the first straight groove 74 is formed toward an upper end of the main mover 40 to form an upper entrance 75 through which the first guide pin 51 may enter the intersection of the first inclined groove 71 and the second inclined groove 72.

In addition, the guide groove 70 further comprises a plurality of second straight grooves 76 formed in parallel with the length direction of the shaft 12. One end of the second straight groove 76 is connected to an intersection of the first inclined groove 71 and the second inclined groove 72 formed at a lower portion of the main mover 40. The other end of the second straight groove 76 is formed toward a lower end of the main mover 40 to form a lower entrance 77.

With such a construction of the main mover 40 and with the help of the first guide pin 51, the main mover 40 may be controlled to move only linearly at some section, without rotation, and to move both linearly and rotationally at some other section. Accordingly, by controlling the linear and rotational motion of the main mover 40 to locate the projection 41 above a desired submover and making the projection 41 press the selected submover, the submover may be linearly moved selectively.

Hereinafter, an operation of a micromanipulator according to an embodiment will be described referring to FIGS. 4A to 4F. FIGS. 4A to 4F schematically illustrate an operation of a micromanipulator according to an embodiment.

In FIGS. 4A to 4F, an operation of moving the projection 41 above the submover 33 and linearly moving the submover 33 downward will be described.

Figure 4A:
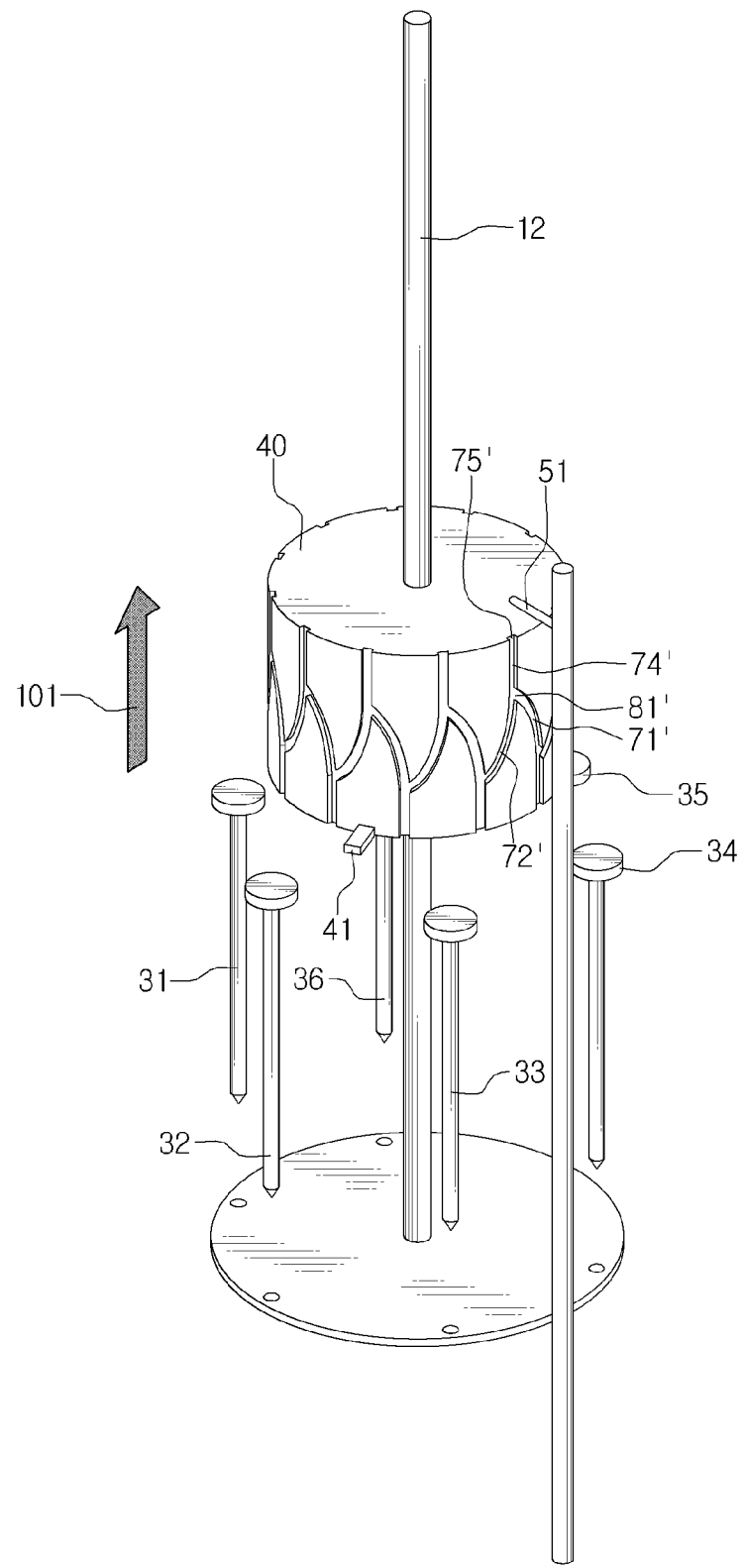
FIGS. 4A, 4B, 4C, 4D, 4E, and 4F schematically illustrate an operation of a micromanipulator according to an embodiment.

First, as illustrated in FIG. 4A, in a state where the first guide pin 51 is located in a straight line with a first straight groove 74' of the main mover 40, the main mover 40 is linearly moved in an upward direction 101. By this operation, the first guide pin 51 passes through an upper entrance 75' and is engaged with the first straight groove 74'. Because the first straight groove 74' is formed to be vertical, the main mover 40 moves only linearly, without rotation, while the first guide pin 51 passes through the first straight groove 74'.

Figure 4B:
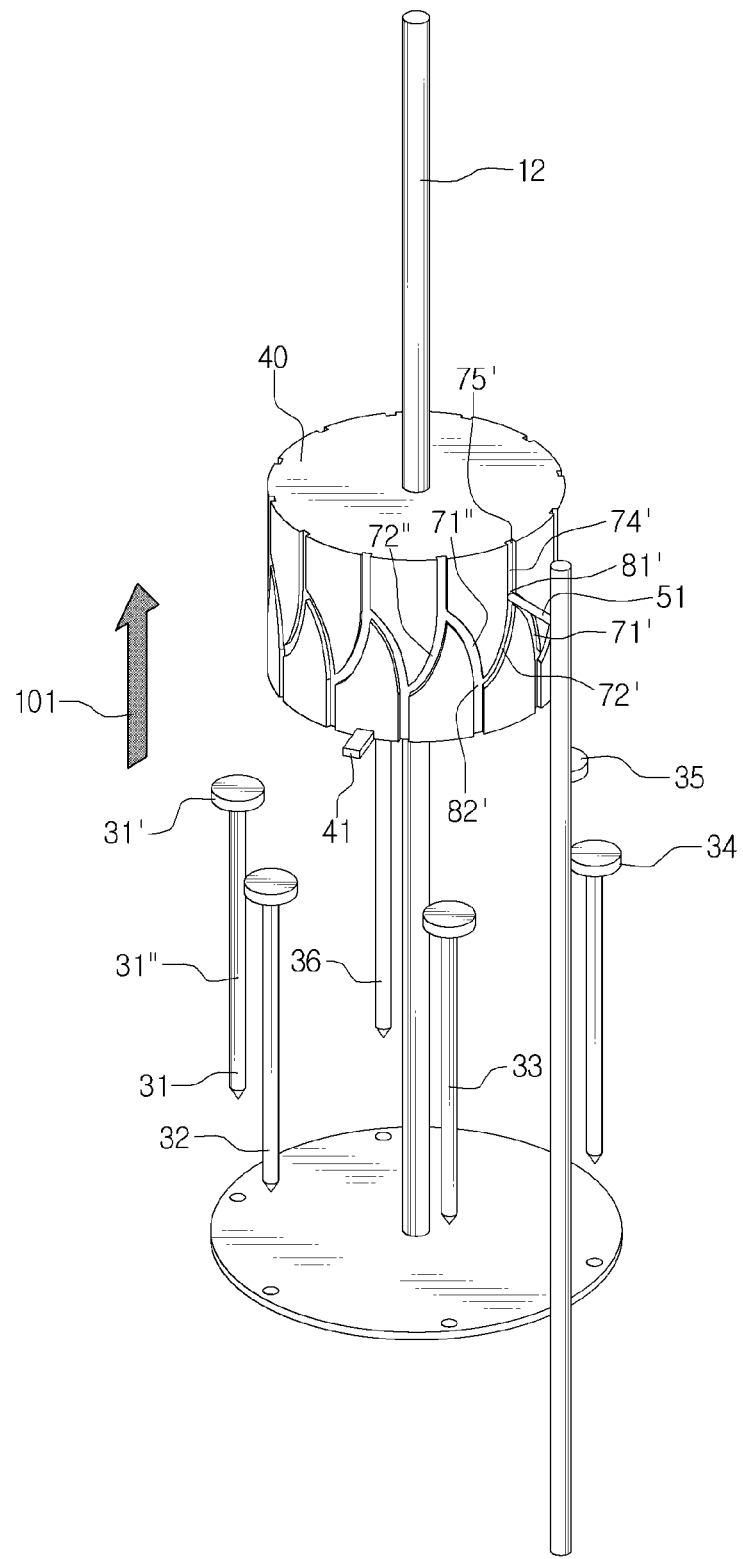

As the main mover 40 further moves in the upward direction 101, the first guide pin 51 reaches an intersection 81' of a first inclined groove 71' and a second inclined groove 72', as illustrated in FIG. 4B.

Figure 4C:
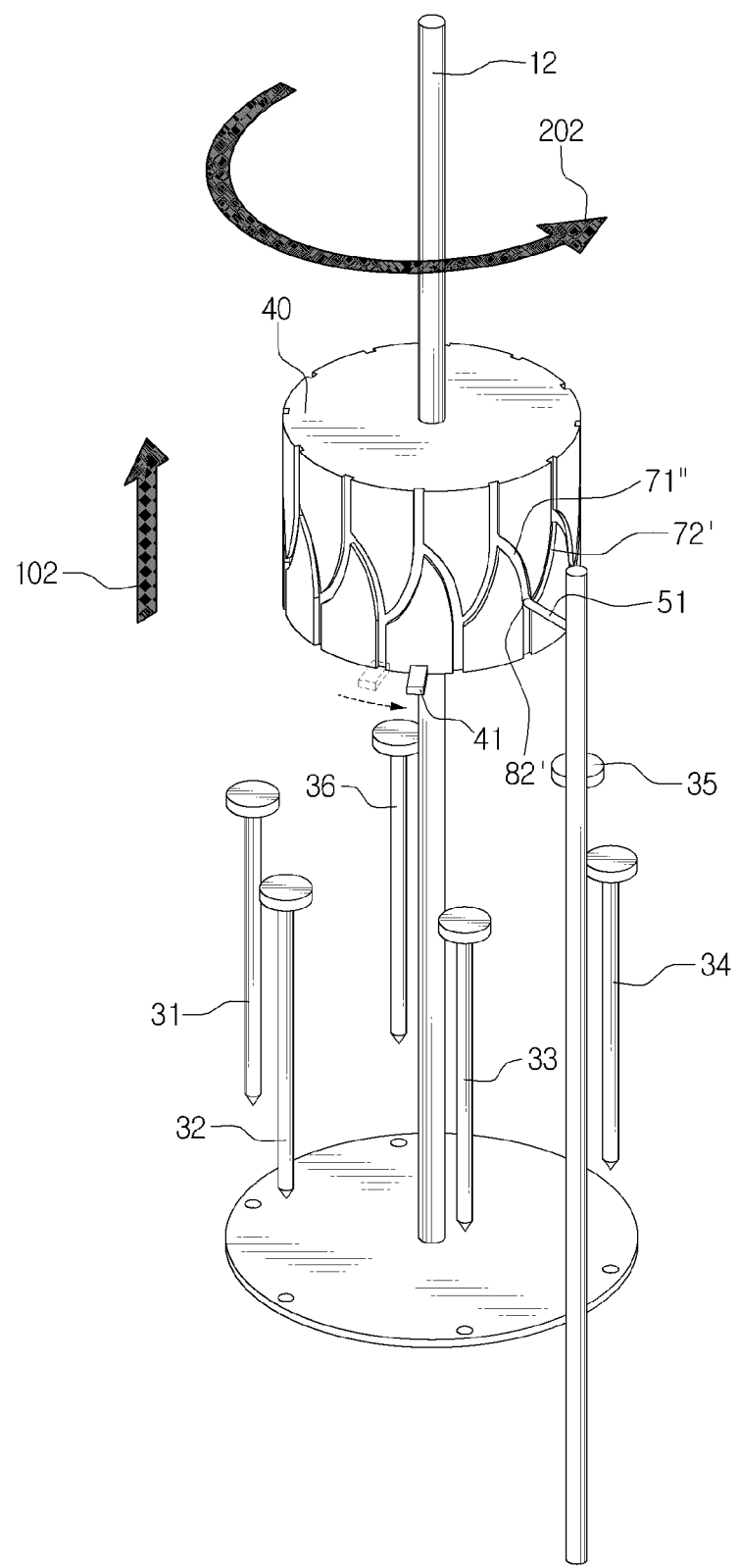

In the embodiment illustrated in FIG. 4A to 4F, the first straight groove 74' and the second inclined groove 72' form a smoothly curved path, whereas the first straight groove 74' and the first inclined groove 71' form a sharply curved path. Accordingly, as illustrated in FIG. 4C, if the main mover 40 further moves linearly in an upward direction 102, the first guide pin 51 moves along the path formed by the second inclined groove 72' to an intersection 82' of the second inclined groove 72' and a first inclined groove 71". By this operation, the main mover 40 rotates in an arrow direction 202, and, accordingly, the lever 41 is rotated from the original location to the location represented by the broken line.

Figure 4D:
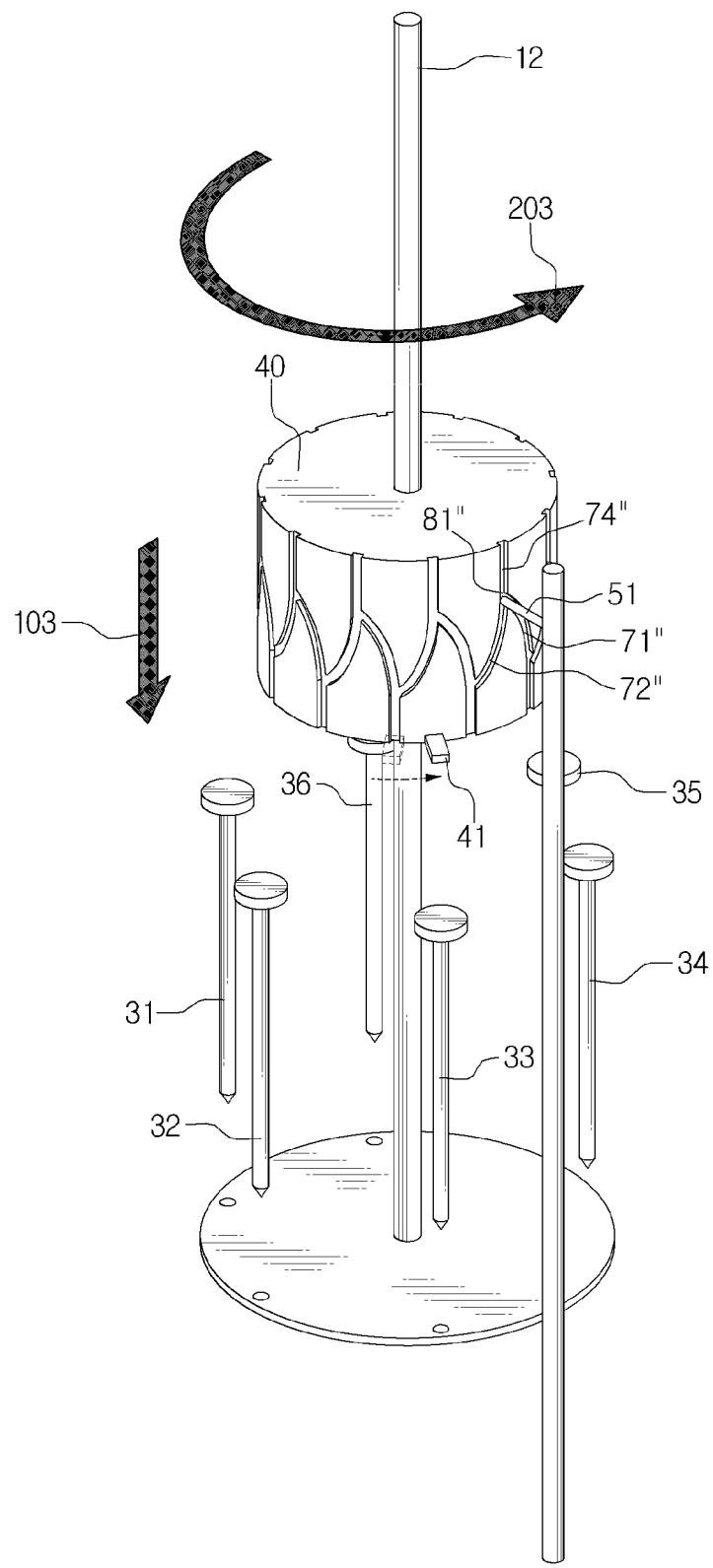

In this state, if the main mover 40 is moved in a downward direction 103, as illustrated in FIG. 4D, the first guide pin 51 moves along a path formed by the first inclined groove 71" and reaches an intersection 81" of the first inclined groove 71" and a second inclined groove 72". By this operation, the main mover 40 rotates in an arrow direction 203, and, accordingly, the projection 41 is rotated from the location represented by the broken line to be located above the submover 33.

If it is desired to select and move a submover other than the submover 33, the above-described upward and downward motion of the main mover 40 is repeated, so that the first guide pin 51 moves sequentially along the paths formed by the first inclined grooves and the second inclined grooves. That is to say, the main mover 40 may be further rotated by repeating the upward and downward motion until the projection 41 is located above the desired submover.

Figure 4E:
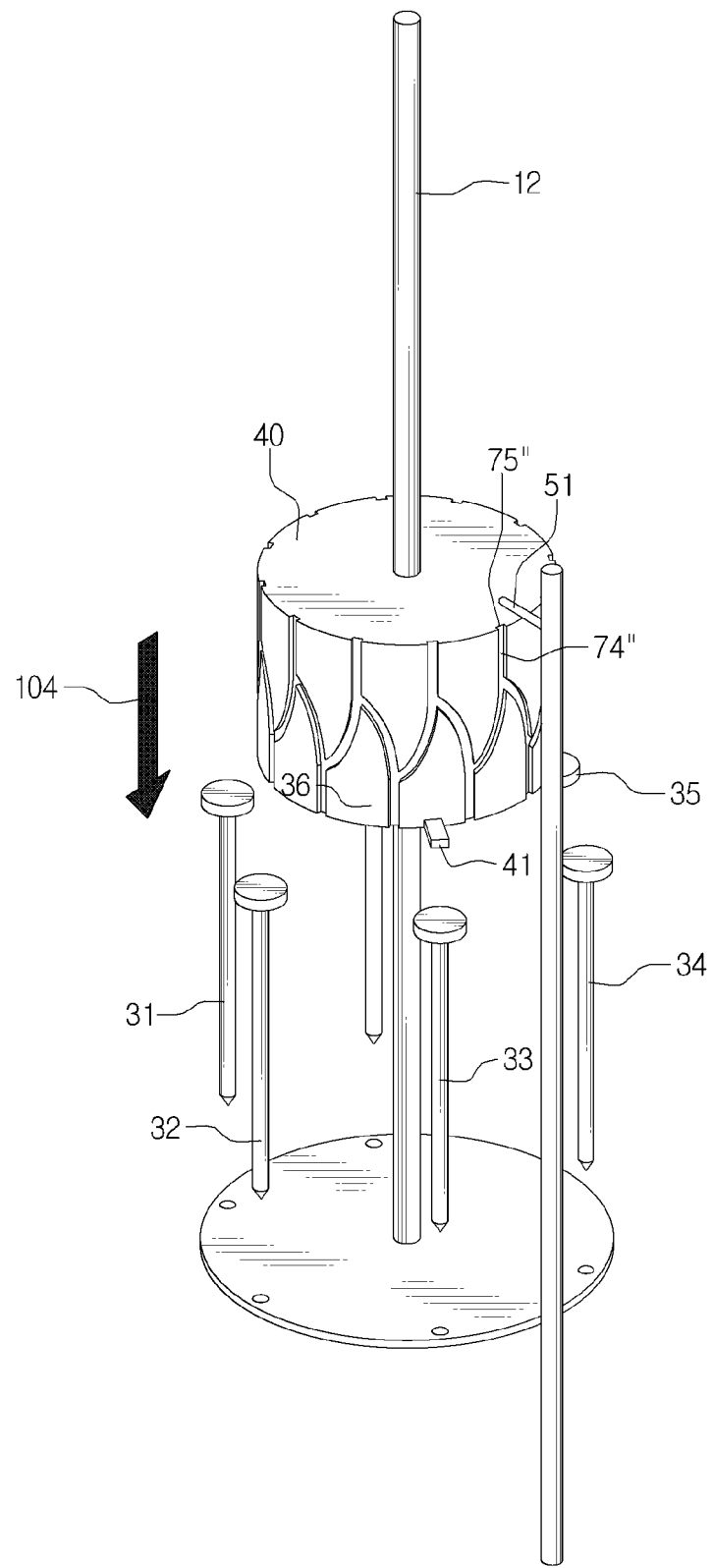

When the lever 41 is located above the submover 33, the main mover 40 is moved in a downward direction 104, as illustrated in FIG. 4E. By this operation, the first guide pin 51 moves along a path formed by a first straight groove 74" and is disengaged from the guide groove through an upper entrance 75".

Because the first straight groove 74" is formed to be straight in a vertical direction, the main mover 40 moves only linearly, without rotation, while the first guide pin 51 passes through the path formed by the first straight groove 74". When the projection 41 contacts with the upper end of the submover 33, the main mover 40 is further moved in a downward direction.

Figure 4F:
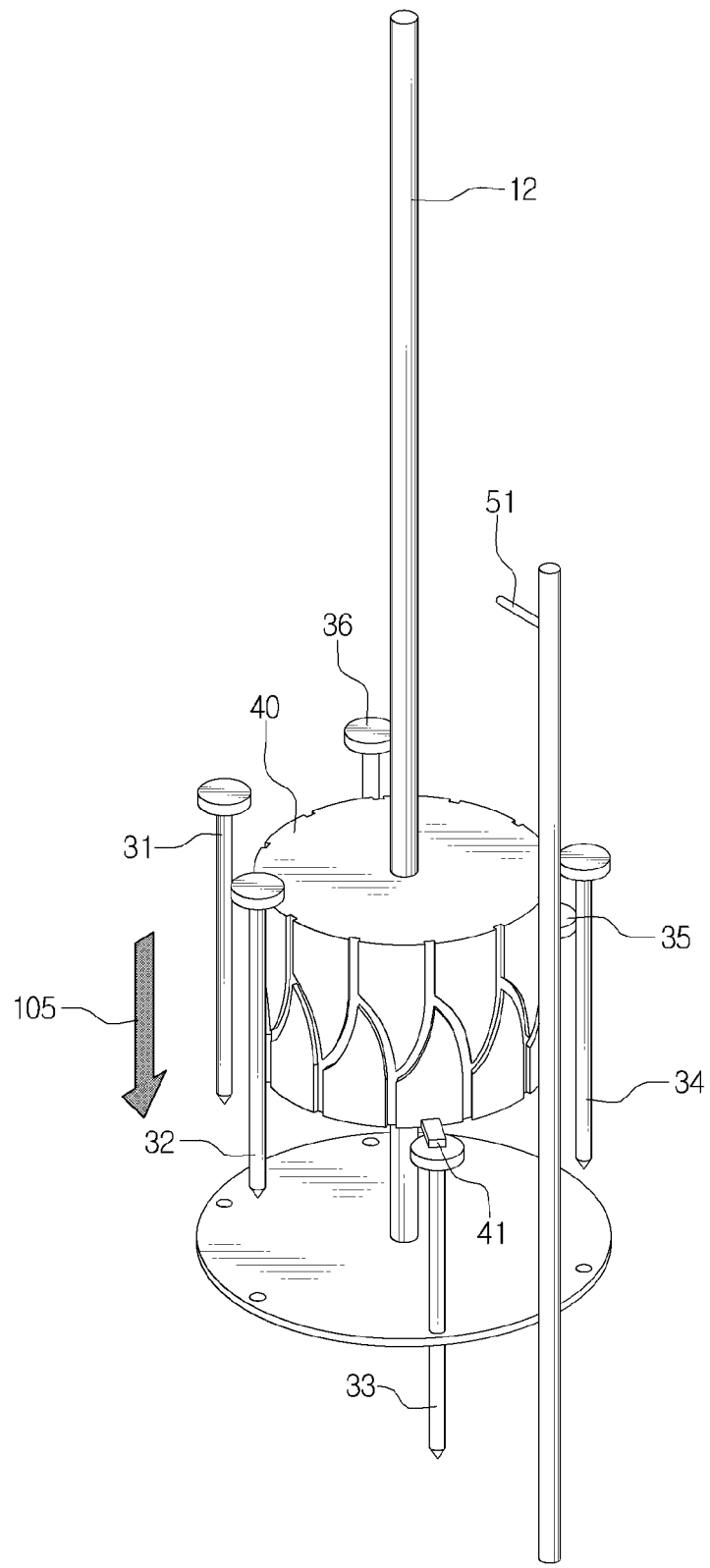

That is, if the main mover 40 is further moved in a downward direction 105, as illustrated in FIG. 4F, the projection 41 presses the upper end of the submover 33, so that the electrode 133 attached on the submover 33 is linearly moved in a downward direction. At this time, the main mover 40 moves only linearly, without rotation, by the operation of the piezo motor 10.

Therefore, according to this embodiment, a plurality of electrodes 131 to 136 may be linearly moved selectively using a single actuator. Accordingly, the multi-selective micromanipulator may have simple structure and high efficiency.

In this embodiment, the main mover 40 rotates in a counterclockwise direction because the first straight groove 74' and the second inclined groove 72' forms a smoothly curved path and the first straight groove 74' and the first inclined groove 71' forms a sharply curved path, as illustrated in FIGS. 4A to 4F. However, this is only exemplary. The first inclined groove 71 and the second inclined groove 72 may be otherwise adequately designed so that the main mover 40 may move in a clockwise direction 200, as illustrated in FIG. 3.

For precise and accurate control of the rotation of the main mover 40 using the guide groove and the guide pin, the design of the guide groove formed on the main mover 40 should be determined depending on the interval between the plurality of submovers.

Accordingly, in an embodiment, the plurality of submovers 31 to 36 are aligned at regular intervals for easier calculation of the rotation angle of the main mover 40. Further, the plurality of first straight grooves 74 and the plurality of second straight grooves 76 (see FIG. 3) are also aligned at regular intervals.

Figure 5:
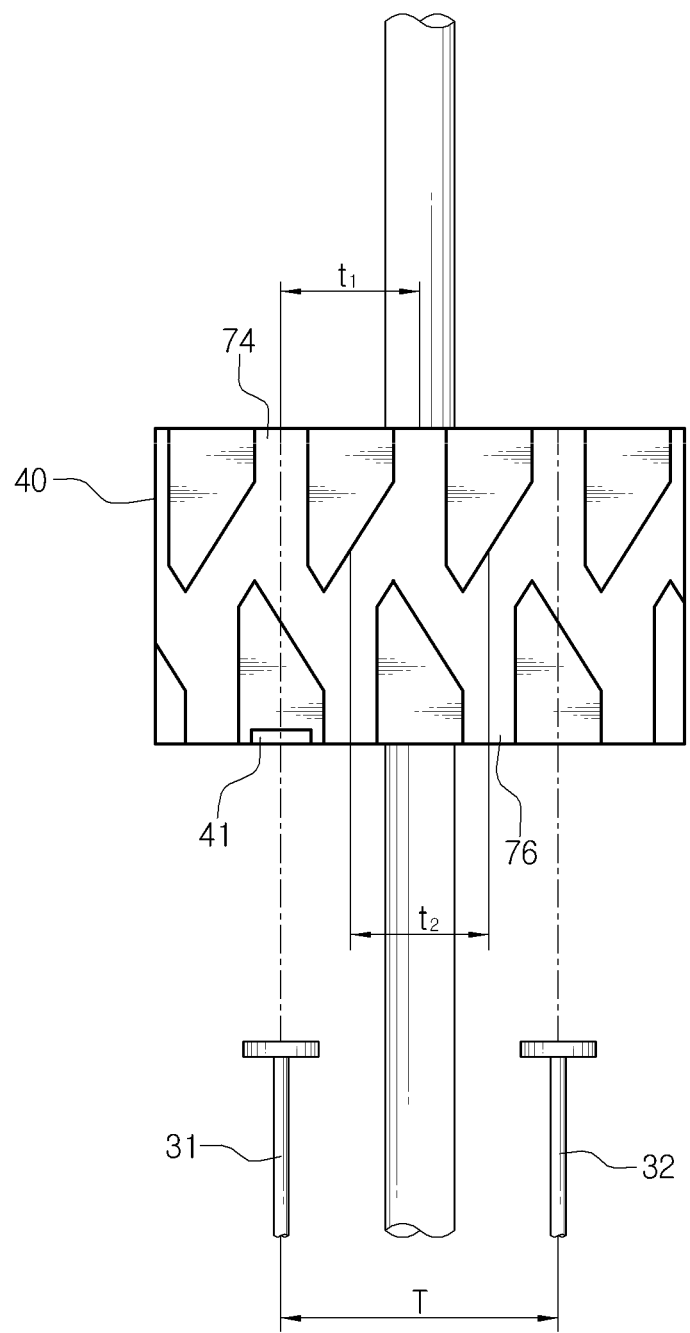
FIG. 5 is a front view illustrating intervals between electrodes, first straight grooves and second straight grooves.

FIG. 5 is a front view illustrating intervals between the submovers, the first straight grooves and the second straight grooves.

As illustrated in FIG. 5, the submovers 31, 32 are spaced apart by a distance T. And, the first straight grooves 74 are spaced apart by a distance $t_1$, and the second straight grooves 76 are spaced apart by a distance $t_2$. In an embodiment, the submovers, the first straight grooves and the second straight grooves are configured to satisfy the relationships $T=2t_1$ and $t_i=t_2$. And, the projection 41 is located in a straight line with one of the first straight grooves 74.

In such a configuration, when the guide pin is engaged with one of the first straight grooves, the projection 41 is necessarily located in a straight line with one of the submovers or in a straight line in the middle of two submovers.

In a state where the projection 41 is located above the submover 31, the projection 41 may be located above the neighboring submover 32 by two reciprocal upward and downward motion of the main mover 40. Such a configuration is advantageous in that the calculation needed to move the projection 41 above the desired submover is markedly simplified.

To use the micromanipulator to move an electrode, which is directly inserted into the body of a subject, the moving distance of the submover including the electrode needs to be precisely and accurately controlled.

In an embodiment, a position sensing device 64 which measures the location and displacement of the main mover 40 is provided for accurate control of the moving distance of the electrode.

Referring to FIG. 2 and FIG. 3 again, a coupling member 62 is connected to the main mover 40. One end of the coupling member 62 is connected to a frame 63 in such a manner that the coupling member 62 may move upward and downward. The other end is connected to the main mover 40 by means of a bearing 60, so that the rotation of the main mover 40 is not interrupted by the coupling member 62. Accordingly, although the coupling member 62 moves upward and downward as the main mover 40 moves upward and downward, the rotation of the main mover 40 is not interrupted by the coupling member 62.

A permanent magnet 61 is fixed at an end of the coupling member 62. A magnetic sensor (not shown) which detects the location of the permanent magnet 61 by measuring the magnetism emitted from the permanent magnet 61 is provided outside the frame 63.

When the main mover 40 moves upward and downward, so does the permanent magnet 61. The magnetic sensor 65 calculates the location of the moving permanent magnet 61 and, based thereon, calculates the current location and displacement of the main mover 40. The location and displacement of the electrodes moved by the main mover 40 may be calculated from the current location and displacement of the main mover 40 considering the original design of the micromanipulator. Accordingly, once the location and displacement of the main mover 40 are calculated, the location of the submovers including the electrodes moved by the main mover 40 may be precisely calculated, and, based on the result, the moving distance of the electrodes may be accurately controlled.

Hereinafter, an operation of linearly moving the submover upward will be described referring to FIGS. 6A to 6E.

FIGS. 6A to 6E schematically illustrate an operation of a micromanipulator according to another embodiment.

Figure 6A:
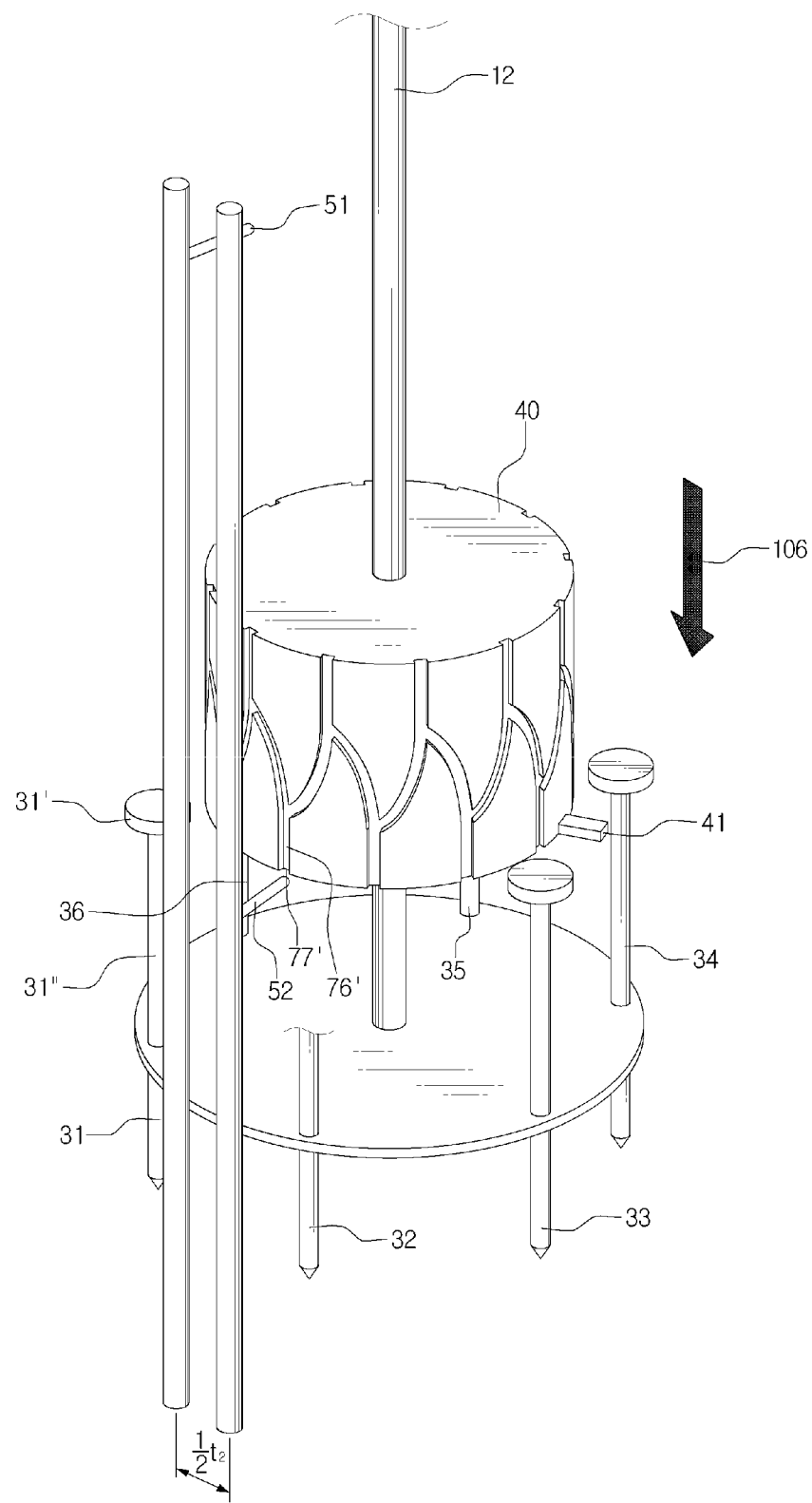
FIGS. 6A, 6B, 6C, 6D, and 6E schematically illustrate an operation of a micromanipulator according to another embodiment.

As illustrated in FIG. 6A, in an embodiment, the submover comprises a plate-shaped head 31' and a body 31" having a diameter smaller than that of the head 31' and extending perpendicularly to the head 31'.

In FIG. 6A, all the submovers 31 to 36 are located at lower positions as pressed by the projection 41. In this embodiment, a second guide pin 52 located below the upper end of the submover is provided to move the submover upward. On the main mover 40, a plurality of second straight grooves 76 are formed (see FIG. 3). One end of the second straight groove 76 is connected to an intersection of the first inclined groove 71 and the second inclined groove 72 formed at a lower portion of the main mover 40, and the other end is formed toward a lower end of the main mover 40 to form a lower entrance 77.

As in the afore-described embodiment, the submovers, the first straight grooves and the second straight grooves are configured to satisfy the relationships $T=2t_1$ and $t_1=t_2$. And, as illustrated in FIG. 6A, the second guide pin 52 is spaced from the first guide pin 51 by ½ $t_2$. As described above, such a configuration is advantageous in that the calculation needed to move the projection 41 above the desired submover is simplified.

First, as illustrated in FIG. 6A, in a state where the second guide pin 52 is located in a straight line with a second straight groove 76' of the main mover 40, the main mover 40 is linearly moved in a downward direction 106. Then, the second guide pin 52 passes through a lower entrance 77' and is engaged with the second straight groove 76'. Because the second straight groove 76' is formed to be vertical, the main mover 40 moves only linearly, without rotation, while the second guide pin 52 passes through the second straight groove 76'.

Figure 6B:
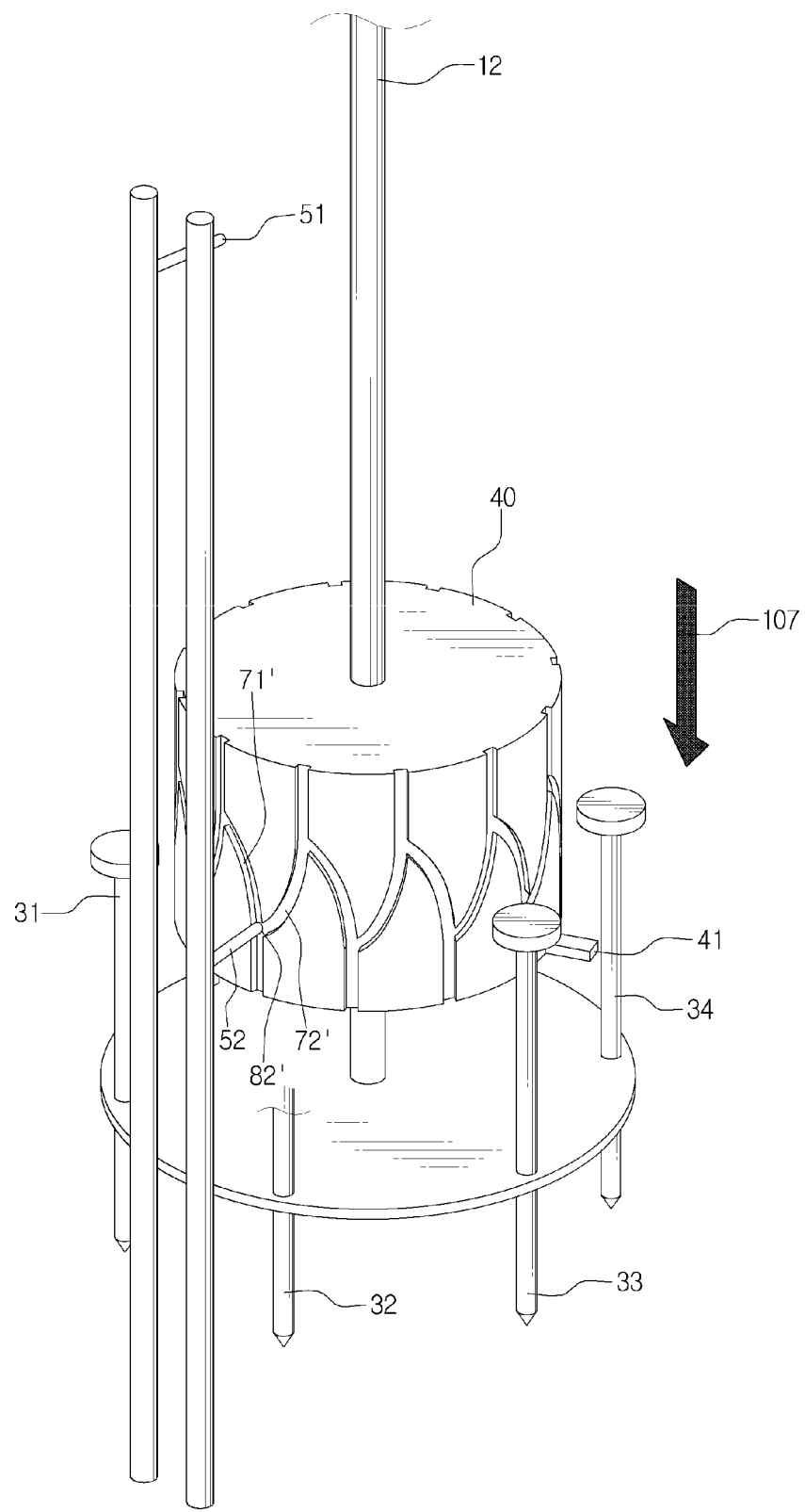

As the main mover 40 further moves in a downward direction 107, the second guide pin 52 reaches an intersection 82' of the first inclined groove 71' and the second inclined groove 72', as illustrated in FIG. 6B.

Figure 6C:
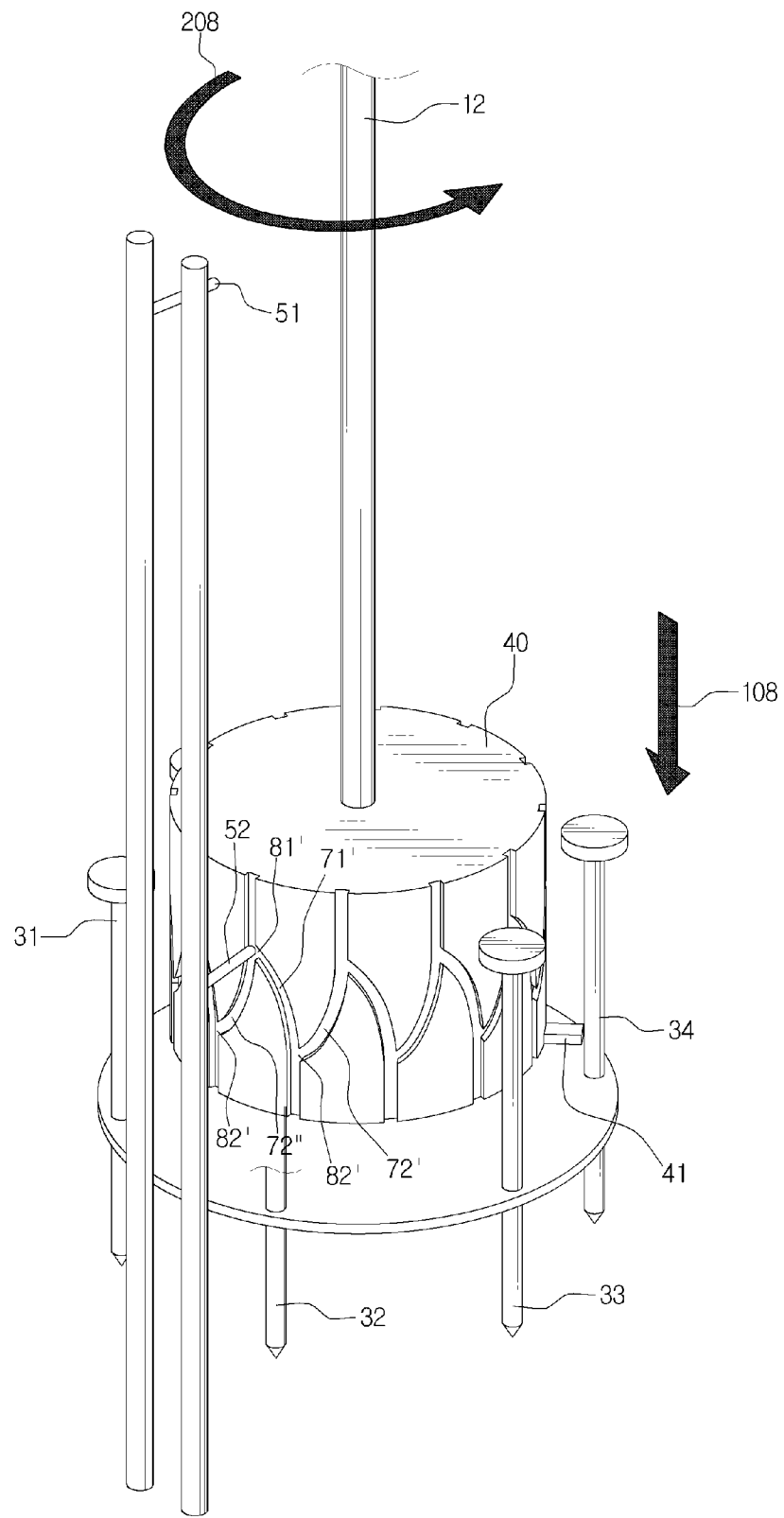

In this state, if the main mover 40 is moved in a downward direction 108, as illustrated in FIG. 6C, the second guide pin 52 moves along a path formed by the first inclined groove 71' and reaches an intersection 81' of the second inclined groove 72" and the first inclined groove 71'. By this operation, the main mover 40 rotates in an arrow direction 208, and, accordingly, the lever projection 41 is also rotated.

Figure 6D:
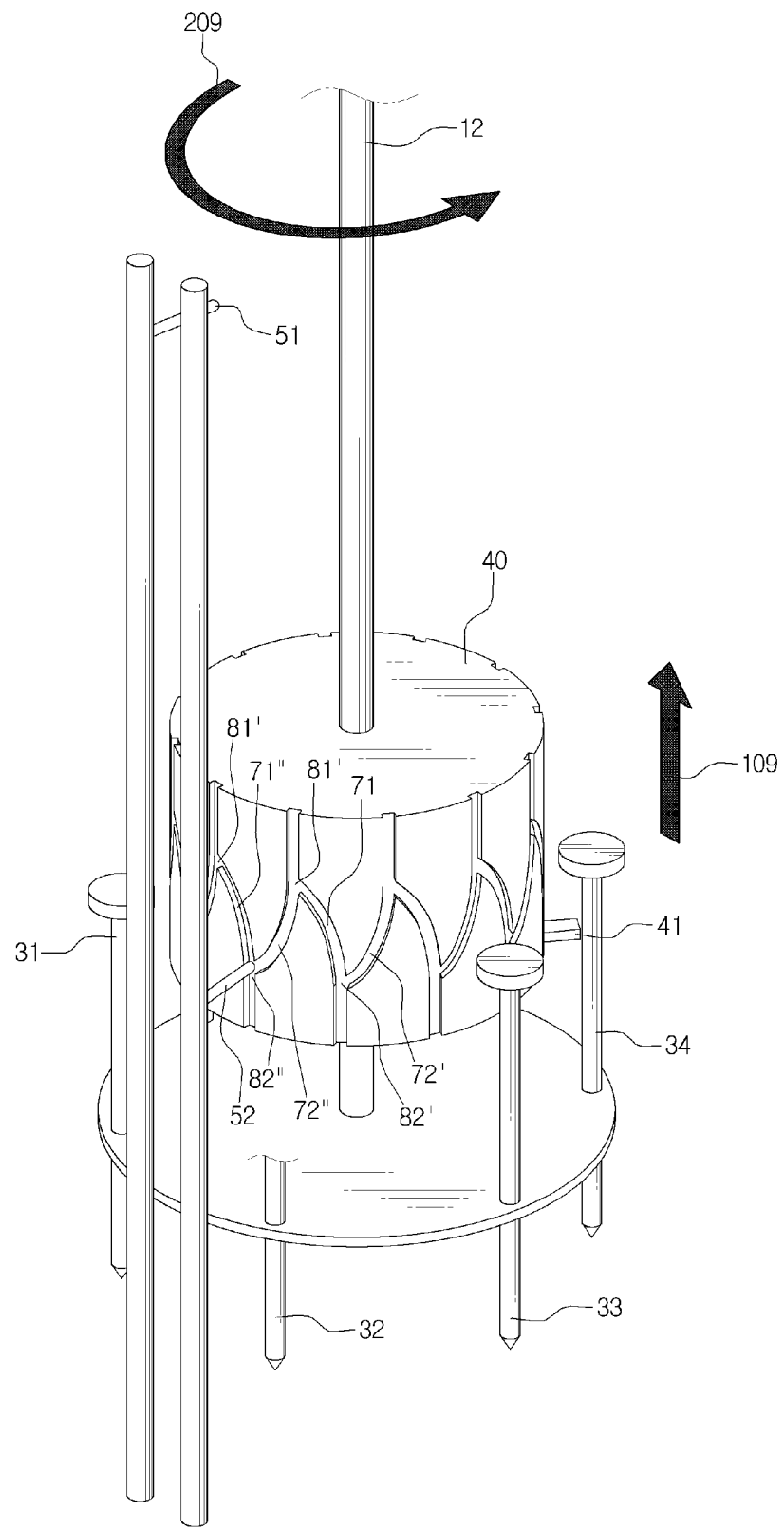

When the main mover 40 is moved in an upward direction 109, as illustrated in FIG. 6D, the second guide pin 52 moves along a path formed by the second inclined groove 72" and reaches an intersection 82" of the first inclined groove 71" and the second inclined groove 72". By this operation, the main mover 40 is further rotated in an arrow direction 209, and the projection 41 is further rotated to be located below the head of the submover 34.

Figure 6E:
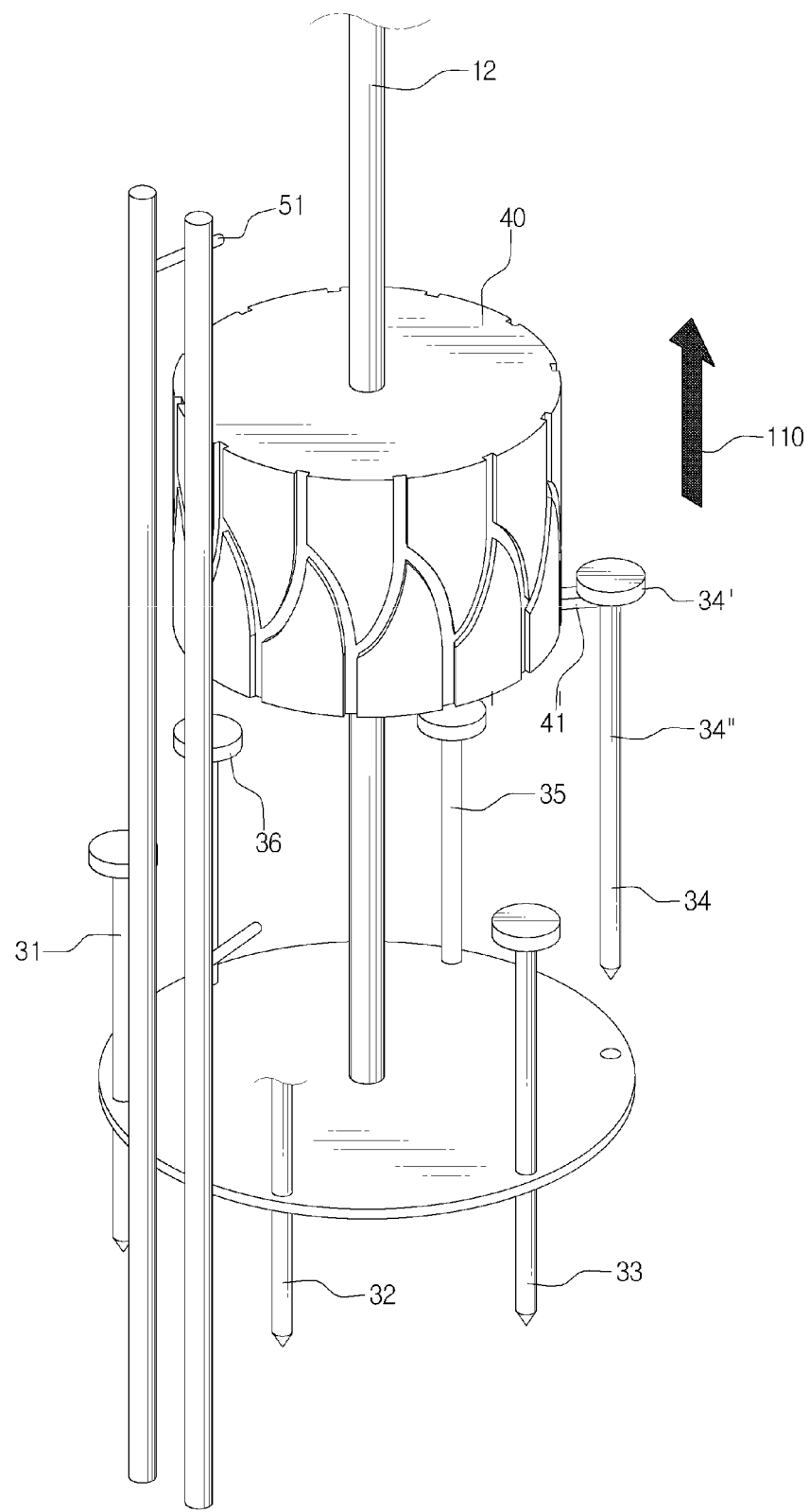

When the main mover 40 is further moved in the upward direction 109, as illustrated in FIG. 6E, the projection 41 pushes the head 34' of the submover 34 and lifts the submover 34 including an electrode 134 in an upward direction.

Although example embodiments of the micromanipulator for selectively moving a plurality of electrodes using a single actuator were described, this disclosure is not necessarily limited thereto. For example, the disclosed micromanipulator may be adequately used to linearly move a plurality of submovers using a single actuator in a microrobot where use of several actuators is restricted.

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

What is claimed is:

1. A multi-selective micromanipulator comprising:
   an actuator including a shaft;
   a main mover which is connected to the shaft and, moves linearly or rotationally with respect to the shaft by the actuator;
   a driving means which moves the main mover;
   a projection which is formed on the main mover; and
   a plurality of submovers which are aligned radially around the shaft,
   wherein the projection selectively contacts with the plurality of submovers depending on the movement of the main mover,
   wherein a selected submover is linearly moved by the projection in a direction parallel to the axis direction,
   wherein:
   the main mover has a cylindrical shape,
   the driving means includes a guide groove formed at a surface of the main mover, and a first guide pin which may be engaged with the guide groove,
   the guide groove comprises a plurality of first inclined grooves formed to be inclined right downwardly with respect to a length direction of the shaft, and a plurality of second inclined grooves formed to be inclined left downwardly with respect to the length direction of the shaft,
   the first inclined grooves and the second inclined grooves are alternately aligned at the side surface of the main mover, and
   a first inclined groove and a second inclined groove adjacent to each other are connected to each other to form a sawtooth-shaped guide pin path.

2. The multi-selective micromanipulator according to claim 1,
   wherein
   the first guide pin is located above the submover,
   the guide groove further comprises a plurality of first straight grooves formed in parallel with the length direction of the shaft, and
   one end of the first straight groove is connected to an intersection of the first inclined groove and the second inclined groove formed at an upper portion of the main mover, and the other end is formed toward an upper end of the main mover to form an upper entrance through which the first guide pin may enter the intersection of the first inclined groove and the second inclined groove.

3. The multi-selective micromanipulator according to claim 2,
   wherein the plurality of submovers are aligned at regular intervals.

4. The multi-selective micromanipulator according to claim 3,
   wherein the plurality of first straight grooves are aligned at regular intervals.

5. The multi-selective micromanipulator according to claim 4,
   wherein the projection is located in a straight line with the first straight groove.

6. The multi-selective micromanipulator according to claim 5,
   wherein, as the main mover moves linearly downward while the projection is located above the submover, the projection presses an upper end of the submover so that the submover is moved linearly downward.

7. The multi-selective micromanipulator according to claim 6,
   wherein
   a second guide pin located below the submover is provided,
   the guide groove further comprises a plurality of second straight grooves formed in parallel with the length direction of the shaft, and
   one end of the second straight groove is connected to an intersection of the first inclined groove and the second inclined groove formed at a lower portion of the main mover, and the other end is formed toward a lower end of the main mover to form a lower entrance through which the second guide pin may enter the intersection of the first inclined groove and the second inclined groove.

8. The multi-selective micromanipulator according to claim 7,
   wherein the plurality of second straight grooves are aligned at regular intervals.

9. The multi-selective micromanipulator according to claim 8, wherein, as the main mover moves linearly upward while the lever is located below the submover, the projection lifts a lower end of the submover so that the submover is moved linearly upward.

10. The multi-selective micromanipulator according to claim 1,
wherein the actuator is a piezo motor.

11. The multi-selective micromanipulator according to claim 1,
wherein
the plurality of submovers include electrodes for detecting electrical signals, and
the electrode extends in a direction parallel to the linear moving direction of the main mover.

12. The multi-selective micromanipulator according to claim 11,
wherein
the plurality of submovers comprises a plate-shaped head and a body having a diameter smaller than that of the head and extending perpendicularly to the head, and
as the main mover moves linearly upward while the projection is located below the submover, the projection lifts the head of the submover so that the submover is moved linearly upward.

13. The multi-selective micromanipulator according to claim 1, further comprising a position sending device which senses the location of the main mover.

14. The multi-selective micromanipulator according to claim 13, wherein the position sensing device comprises a magnet fixed to the main mover and a magnetic sensor which senses the location of the magnet.

* * * * *